US00PP35657P2

(12) United States Plant Patent
Ackerman et al.

(10) Patent No.: US PP35,657 P2
(45) Date of Patent: Feb. 20, 2024

(54) STRAWBERRY PLANT NAMED 'PE-14.145.059'

(50) Latin Name: ***Fragaria* x *ananassa***
Varietal Denomination: PE-14.145.059

(71) Applicant: Plant Sciences, Inc., Watsonville, CA (US)

(72) Inventors: Stephen M. Ackerman, Salinas, CA (US); Steven D. Nelson, Watsonville, CA (US); Michael D. Nelson, Watsonville, CA (US)

(73) Assignee: Plant Sciences, Inc., Watsonville, CA (US)

( * ) Notice: Subject to any disclaimer, the term of this patent is extended or adjusted under 35 U.S.C. 154(b) by 0 days.

(21) Appl. No.: 18/143,369

(22) Filed: May 4, 2023

(51) Int. Cl.
*A01H 5/02* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409; A01H 5/02
See application file for complete search history.

(56) References Cited

U.S. PATENT DOCUMENTS

PP28,756 P3 12/2017 Ackerman et al.

*Primary Examiner* — Keith O. Robinson
(74) *Attorney, Agent, or Firm* — Foley & Lardner LLP

(57) ABSTRACT

This invention relates to a new and distinct variety of strawberry plant named 'PE-14.145.059'. This new strawberry plant named 'PE-14.145.059' is primarily adapted to the growing conditions of the central coast of California, and is primarily characterized by its orange red to red fruit color, medium fruit size, conical fruit shape and no difference to very slight difference in fruit shape; very attractive fruit with good flavor, medium to firm flesh, with seeds held level with the surface; large plant size which produces an abundance of runners; small foliage size, medium to yellow green in color, and concave in cross section; fruiting trusses with little to no anthocyanins which are weakly pubescent and held even with the foliage.

5 Drawing Sheets

Latin name of the genus and species of the plant claimed: *Fragaria* x *ananassa.*

Variety denomination: 'PE-14.145.059'.

BACKGROUND OF THE INVENTION

The present invention relates to a new and distinct strawberry variety named 'PE-14.145.059'. This new variety is a result of a controlled cross made in 2014 in an ongoing breeding program between strawberry selection designated 'PE-3.89.089' (not patented) as the seed (female) parent, and strawberry selection designated 'PE-7.2064' (not patented) as the pollen (male) parent. The variety is botanically known as *Fragaria* x *ananassa.*

The seedling resulting from the aforementioned cross was selected from a controlled breeding plot in Ventura County, California in the fall of 2016. After its selection, the new variety was asexually propagated by stolons in Siskiyou and San Joaquin Counties, California. The new variety was tested extensively over the next several years in fruiting fields in Ventura County, California. This propagation has demonstrated that the combination of traits disclosed herein as characterizing the new variety are fixed and remain true-to-type through successive generations of asexual reproduction.

BRIEF SUMMARY OF THE INVENTION

'PE-14.145.059' is primarily adapted to the climate and growing conditions of the central coast of California. The nearby Pacific Ocean provides the humidity and moderate temperatures needed to produce a strong, vigorous plant and maintain fruit quality during the fall production months.

The following traits have been repeatedly observed and are determined to be unique characteristics of 'PE-14.145.059', which in combination distinguish this strawberry plant as a new and distinct variety:

1. Fruit is orange red to red in color, medium in size, conical in shape, with no difference to very slight difference in fruit shape;
2. Fruit is very attractive with very good flavor, has medium to firm flesh, with seeds held level with the surface;
3. Plant is large in size and produces an abundance of runners;
4. Foliage is small in size, medium to yellow green in color, and concave in cross section; and
5. Fruiting trusses have little to no anthocyanins, are weakly pubescent and held even with the foliage.

The strawberry variety that is believed to be most closely related to the new variety 'PE-14.145.059' is 'PE-7.2059' (U.S. Plant Pat. No. 28,756). In side-by-side comparisons to the similar strawberry variety 'PE-7.2059', 'PE-14.145.059' differs by the following combination of characteristics as described in Table 1.

TABLE 1

| Characteristic | 'PE-14.145.059' | 'PE-7.2059' (U.S. Plant Pat. No. 28,756) |
|---|---|---|
| Fruit: color | Ranges from orange red to red | Red |
| Fruit: size (length × width ratio) | As long as broad | Slightly longer than broad |
| Fruit: marketable yield, season average (grams/plant) | 800 | 585 |
| Fruit: insertion of achenes | Level with the surface | Ranges from level to above the surface |
| Fruit: flavor | Very good | Good |
| Plant: size | Large | Medium |
| Stolon: anthocyanin intensity | Strong | Absent or very weak |
| Foliage: terminal leaflet size (length × width ratio) | Broader than long | Longer than broad |
| Disease and pest reactions: Fusarium wilt | Resistant | Susceptible |

For identification, a series of molecular markers have been determined for this new variety.

'PE-14.145.059' differs from its parents, 'PE-3.89.089' and 'PE-7.2064' by the following combination of characteristics as described in Tables 2 and 3.

TABLE 2

| Characteristic | 'PE-14.145.059' | 'PE-3.89.089' (not patented) |
|---|---|---|
| Fruit: shape | Conical | Globose |
| Fruit: size | Medium | Very small |
| Plant: size | Large | Medium |
| Stolon: quantity | Many | Medium |
| Disease: Fusarium wilt | Resistant | Susceptible |

TABLE 3

| Characteristic | 'PE-14.145.059' | 'PE-7.2064' (not patented) |
|---|---|---|
| Fruit: size | Medium | Small |
| Fruit: insertion of achenes | Level with the surface | Ranges from level to below the surface |
| Fruit: flavor | Very good | Fair |
| Plant: size | Large | Medium |
| Stolon: quantity | Many | Medium |

BRIEF DESCRIPTIONS OF THE PHOTOGRAPHS

The accompanying color photographs illustrate the overall appearance of typical specimens of the new strawberry variety 'PE-14.145.059' at various stages of development, as true as it is reasonably possible with color reproductions of this type. Color in the photographs may differ slightly from the color value cited in the botanical descriptions which accurately describe the color of 'PE-14.145.059'. The depicted plant and plant parts of the new strawberry variety 'PE-14.145.059' are approximately three to four months old. The photographs were taken in Ventura County, California.

DETAILED BOTANICAL DESCRIPTION

Figure 1:
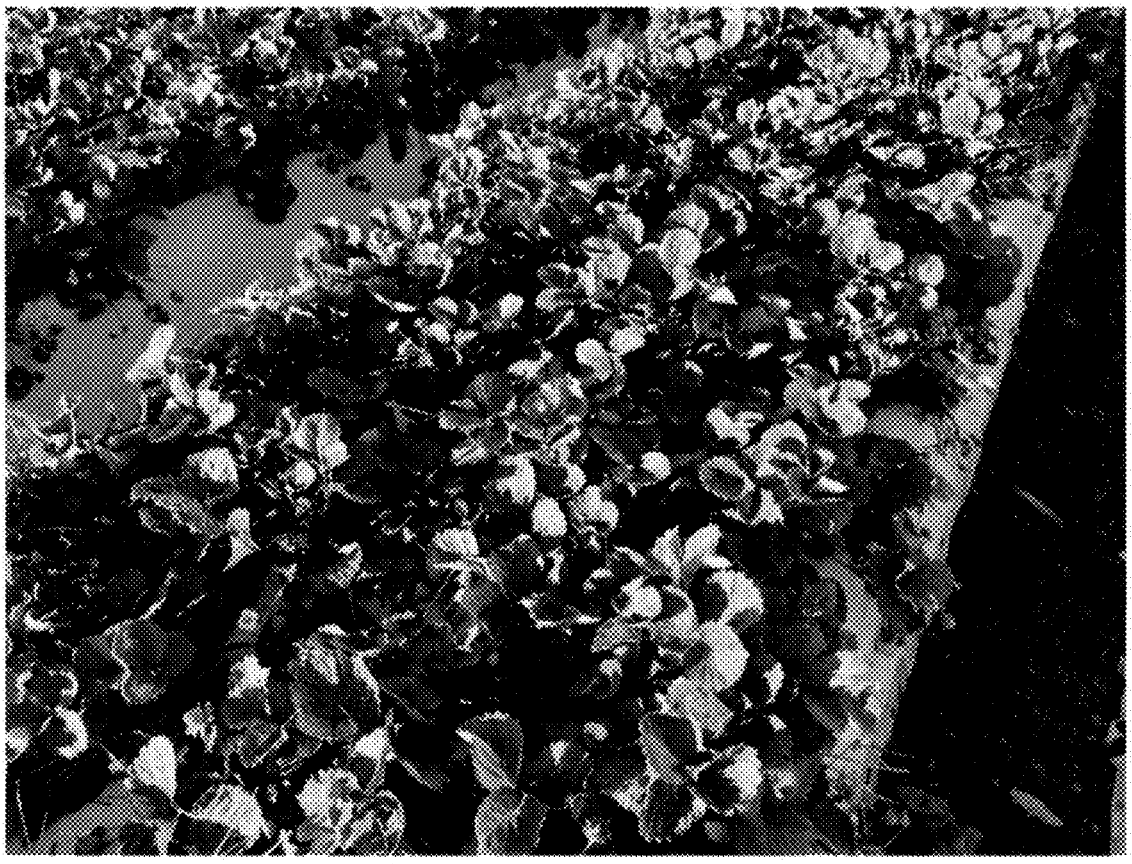
FIG. 1 shows fruiting field characteristics of 'PE-14.145.059', taken in the month of November 2022.
Figure 2:
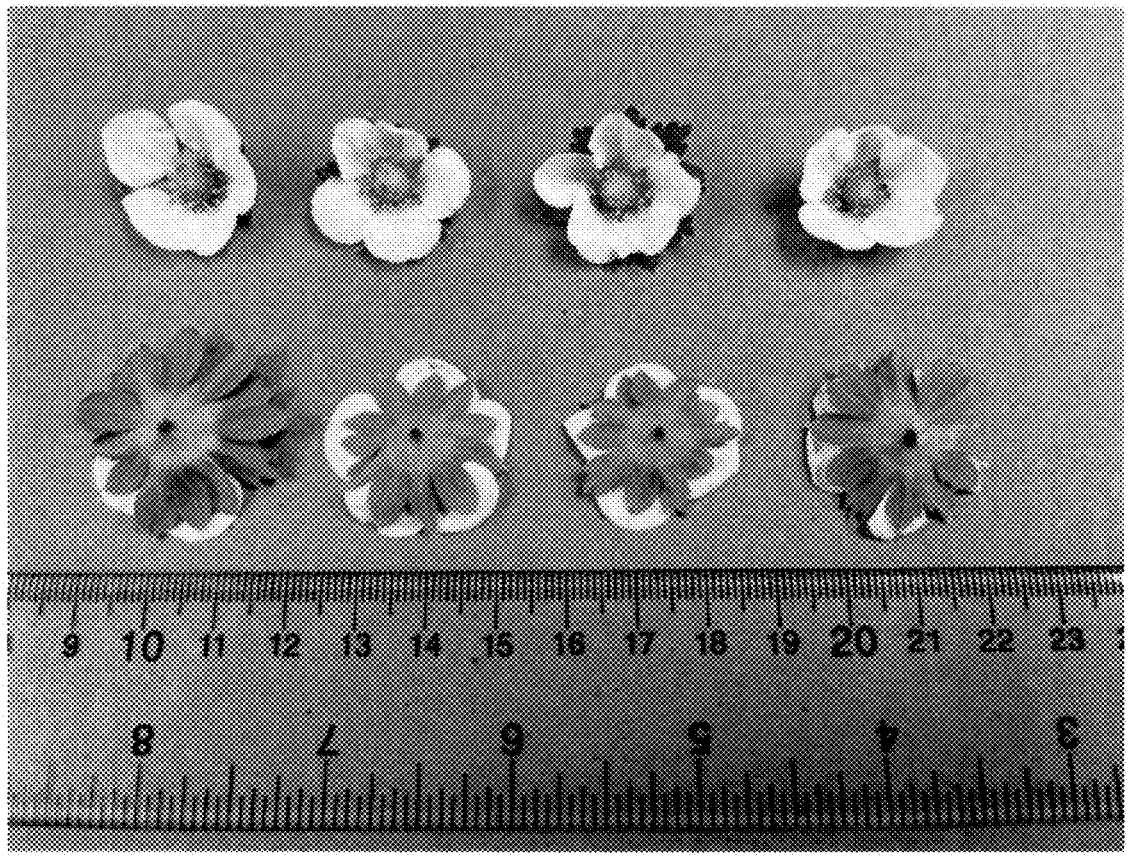
FIG. 2 shows upper and lower surfaces of flower and flower parts of 'PE-14.145.059', taken in the month of November 2022.
Figure 3:
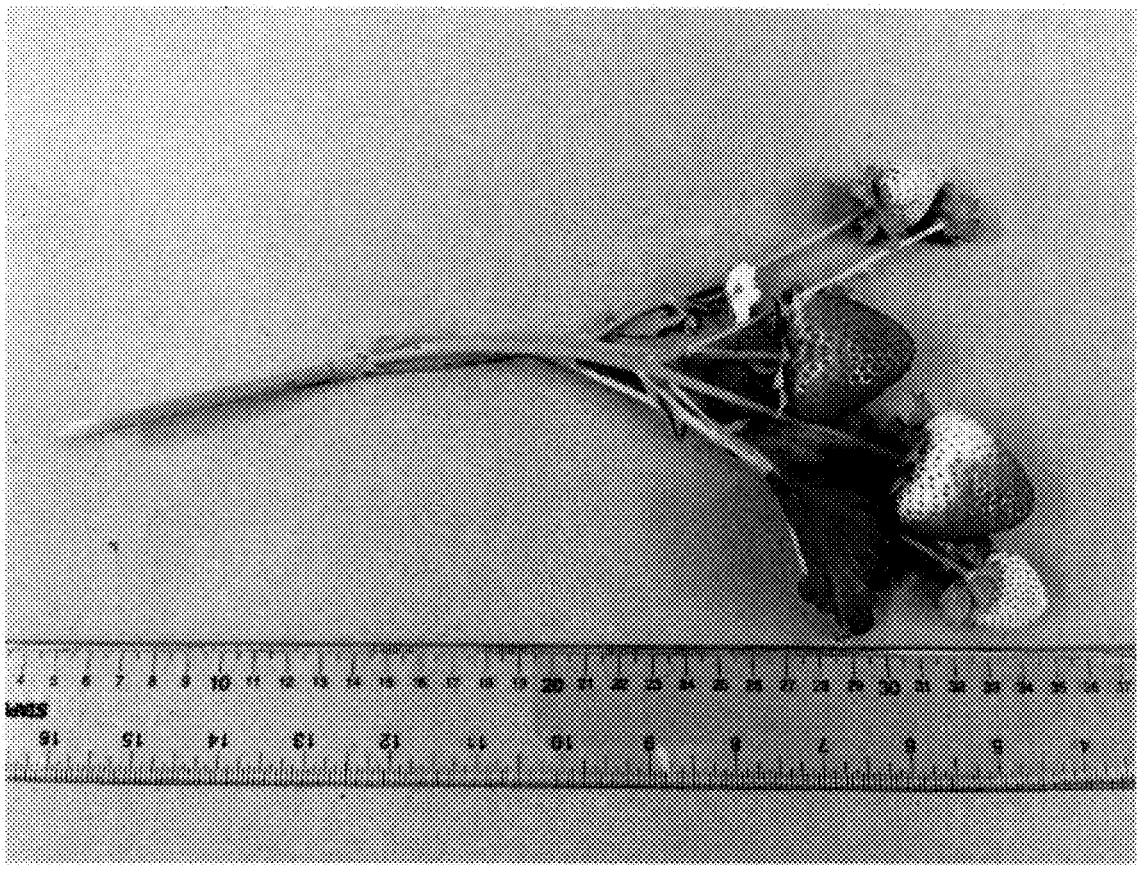
FIG. 3 shows typical fruiting truss and truss parts of 'PE-14.145.059', taken in the month of November 2022.
Figure 4:
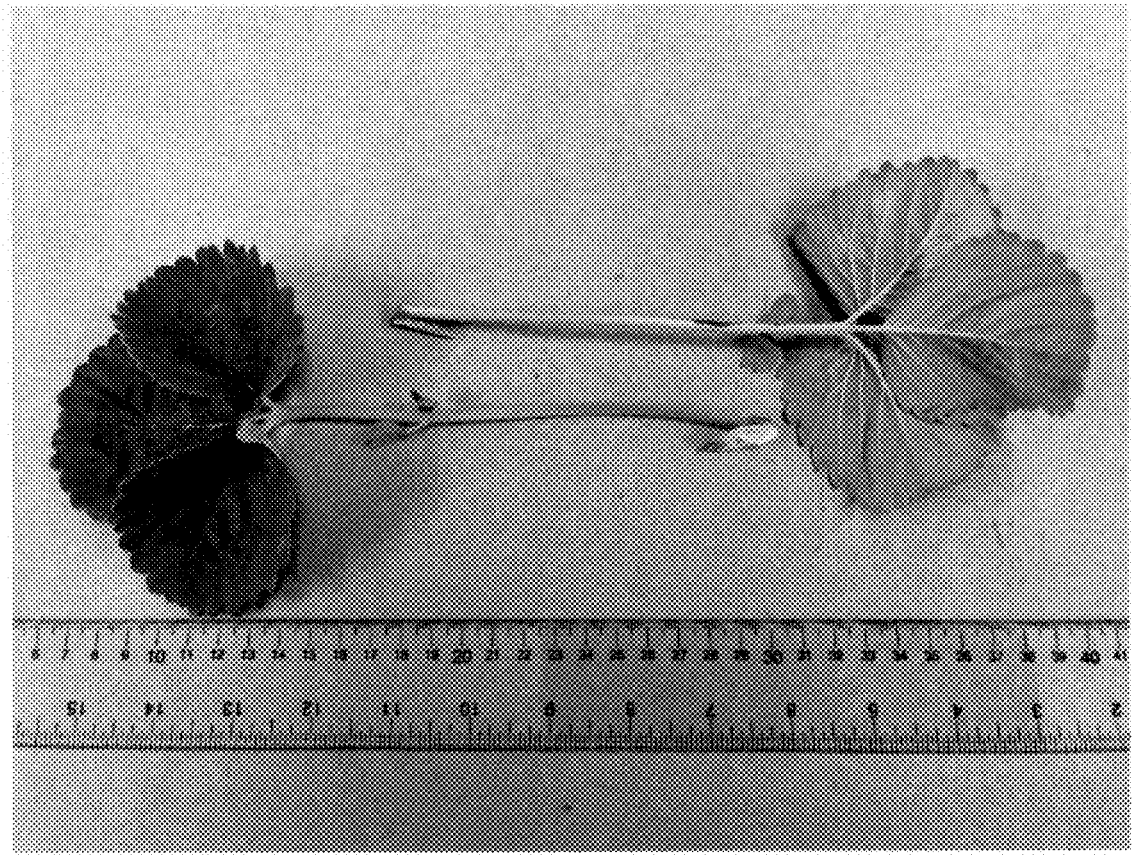
FIG. 4 shows upper and lower surfaces of leaf and leaf parts of 'PE-14.145.059', taken in the month of November 2022.
Figure 5:
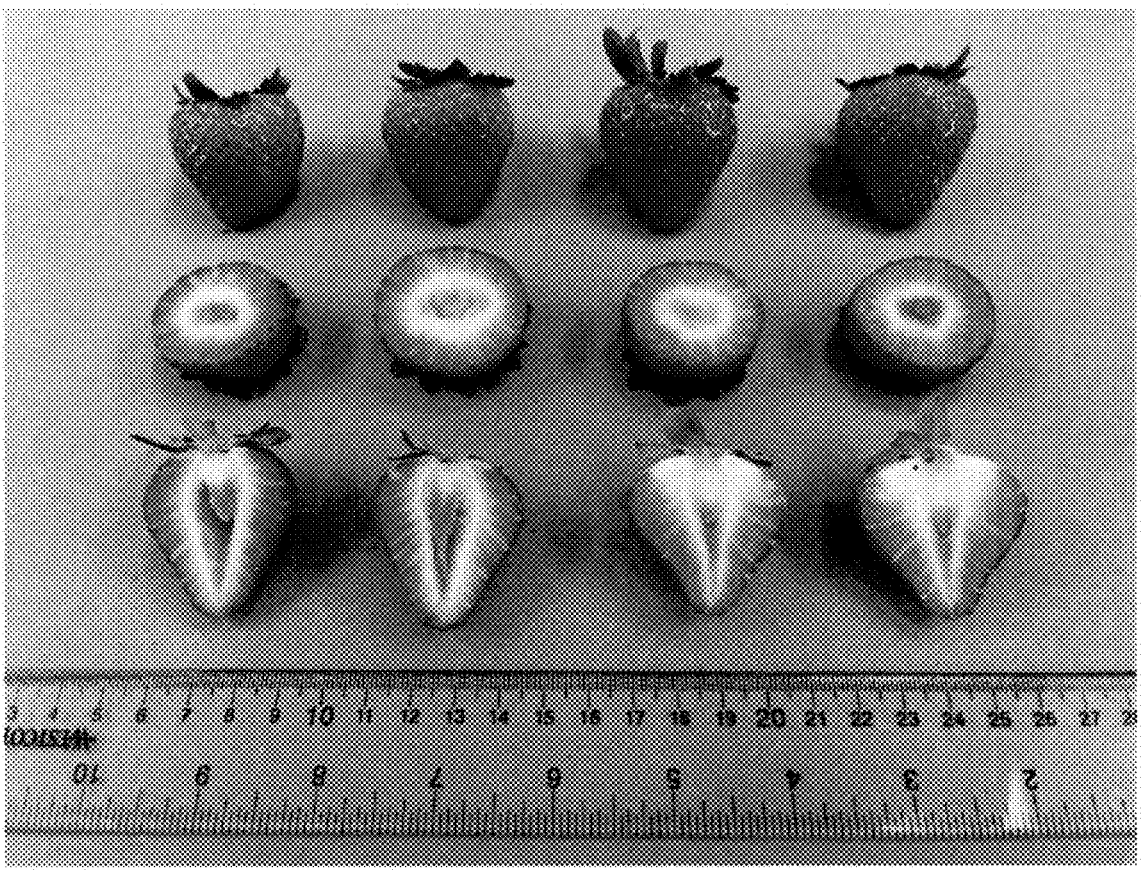
FIG. 5 shows internal and external mature fruit characteristics of 'PE-14.145.059', taken in the month of November 2022.

The new variety 'PE-14.145.059' has not been observed under all possible environmental conditions. The characteristics of the new variety 'PE-14.145.059' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'PE-14.145.059', unless otherwise noted, are based on observations taken during the 2022 growing season in Ventura County, California. These measurements and ratings were taken from plants of 'PE-14.145.059' dug from a low-elevation nursery located in San Joaquin County, California in January 2022 and planted approximately six months later in Ventura County, California. The approximate age of the observed plants is three to four months. Yield observations including average weight and marketable yield, along with fruit quality characteristics including soluble solids, are averaged from five years of data collected from the 2018 through 2022 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London, Sixth Edition (2015).

The following characteristics describe fruit, plant, stolon, foliage, fruiting truss, flower, reproductive organs and pest and disease characteristics of the new strawberry 'PE-14.145.059'.

Fruit characteristics:

*Color of mature fruit*.—RHS 45B (ranges from orange red to red).

*Color of internal flesh*.—RHS 43A (ranges from light red to medium red).

*Color of core*.—RHS 43C (medium red).

*Average length* (*cm*).—3.7.

*Average width* (*cm*).—3.6.

*Size*.—Medium.

*Average length/width ratio*.—1.02 (as long as broad).

*Hollow center average length* (*mm*).—11.4.

*Hollow center average width* (*mm*).—5.2.

*Hollow center expression*.—Ranges from weak to moderate.

*Season average weight* (*gm*).—23.1.
*Marketable yield season* (*gm/plant*).—800.
*Predominant shape*.—Conical.
*Difference in shape between primary and secondary fruit*.—None or very slight.
*Band without achenes*.—Absent or very narrow.
*Evenness of surface*.—Even or very slightly uneven.
*Evenness of color*.—Even or very slightly uneven.
*Glossiness*.—Ranges from medium to strong.
*Insertion of achenes*.—Level with surface.
*Average calyx diameter* (*cm*).—4.2.
*Position of calyx attachment*.—Inserted.
*Attitude of sepals*.—Outward.
*Size of calyx in relation to fruit diameter*.—Slightly larger.
*Adherence of calyx* (*when fully ripe*).—Strong.
*Firmness of flesh*.—Ranges from medium to firm.
*Keeping quality*.—Very good.
*Fruit market*.—Fresh.
*Post-harvest fruit longevity* (*at* 1 *to* 3 *degrees celsius*).—7 to 10 days.
*Distribution of red color of the flesh*.—Marginal and central.
*Flavor*.—Very good.
*Soluble solids* (% *brix*).—8.6.
*Achene color, shaded side*.—RHS 160A (greyed yellow group).
*Achene color, sun-exposed side*.—RHS 182A (greyed red group).
*Achene average length* (*mm*).—1.6.
*Achene average width* (*mm*).—0.8.
*Achene average weight* (*mg*).—0.59.
*Achene average quantity per berry*.—349.
*Achene shape*.—Elliptic.
*Flowering season* (50% *of plants with at least one flower*).—Early (August in Ventura County, California).
*Maturing season* (50% *of plants with mature fruit*).—Early (September in Ventura County, California).
*Flowering season*.—August to December (in Ventura County, California).
*Harvest season*.—September to January (in Ventura County, California).
*Harvest maturity*.—October (in Ventura County, California).
*Plant hardiness*.—Zone 10 (USDA Plant Hardiness Zone Map).
*Type of bearing*.—Fully remontant (non-flowering runners).

Plant characteristics:
*Average height* (*cm*).—27.6.
*Average spread* (*cm*).—38.3.
*Size*.—Large.
*Habit*.—Semi-upright.
*Density*.—Ranges from medium to dense.
*Vigor*.—Strong.

Stolon characteristics:
*Color*.—RHS 146D (yellow green group).
*Anthocyanin coloration*.—RHS 181A (greyed red group).
*Anthocyanin intensity*.—Strong.
*Pubescence*.—Medium.
*Attitude of hairs*.—Upward.
*Average quantity in nursery* (*per square foot*).—8 to 10 (many).
*Average diameter at first bract* (*mm*).—3.0 (medium).
*Length from mother plant to first daughter* (*cm*).—29.8.

Terminal leaflet characteristics:
*Average length* (*cm*).—7.3.
*Average width* (*cm*).—7.9.
*Average area terminal* ($cm^2$).—58.1.
*Average length/width ratio*.—0.93 (broader than long).
*Shape of base*.—Rounded.
*Shape of apex*.—Obtuse.
*Margins* (*shape of teeth*).—Rounded (crenate).
*Average serrations per leaf*.—21.1.

Foliage characteristics:
*Color of upper surface*.—RHS 146A (medium yellow green).
*Color of lower surface*.—RHS 147C (yellow green group).
*Color of venation, upper surface*.—RHS 146C (yellow green group).
*Color of venation, lower surface*.—RHS 145A (yellow green group).
*Number of leaflets*.—3.
*Leaf size*.—Small.
*Average length* (*cm*).—11.7.
*Average width* (*cm*).—14.1.
*Average area foliage* ($cm^2$).—165.4.
*Shape in cross section*.—Strongly to slightly concave.
*Interveinal blistering*.—Strong.
*Texture of upper surface*.—Medium.
*Texture of lower surface*.—Smooth.
*Venation pattern*.—Pinnate reticulate.
*Leaf glossiness*.—Medium.
*Leaf variegation*.—Absent.

Petiole characteristics:
*Petiole color*.—RHS 144B (yellow green group).
*Petiole average length* (*cm*).—18.4.
*Petiole average diameter* (*mm*).—3.5.
*Attitude of hairs*.—Slightly outward.
*Frequency of bract leaflets*.—64% occurrence (mostly).
*Size of bract leaflets*.—Medium.
*Pubescence*.—Sparse.
*Petiolule color*.—RHS 144B (yellow green group).
*Petiolule average length* (*mm*).—16.8.
*Petiolule average diameter* (*mm*).—2.0.

Stipule characteristics:
*Color*.—RHS 146B (yellow green group).
*Anthocyanin coloration*.—RHS 60B (red purple group).
*Anthocyanin intensity*.—Absent or very weak.
*Average length* (*mm*).—2.0.
*Average width* (*mm*).—9.0.
*Shape*.—Triangular.
*Texture*.—Light.
*Shape of base*.—N/A.
*Shape of apex*.—Acute.
*Margins*.—Entire (smooth).

Fruiting truss characteristics:
*Anthocyanin coloration*.—RHS 181B (greyed red group).
*Anthocyanin intensity*.—Absent or very weak.
*Average length at maturity* (*cm*).—27.2.
*Position relative to foliage*.—Level with.
*Flower quantity* (*season average per plant*).—40.2 (medium).
*Average fruit quantity per truss*.—6.0 (medium).
*Attitude at first pick*.—Prostrate.

*Primary pedicel color*.—RHS 144B (yellow green group).
*Primary pedicel average length* (*cm*).—10.9.
*Primary pedicel average diameter* (*mm*).—2.9.
*Pedicel attitude of hairs*.—Upward.
*Pedicel texture*.—Weak.
*Primary peduncle color*.—RHS 144B (yellow green group).
*Primary peduncle average length* (*cm*).—6.8.
*Primary peduncle average diameter* (*mm*).—5.1.
*Peduncle texture*.—Medium.

Flower characteristics (secondary unless indicated):
*Petal color, upper surface*.—RHS NN155C (white group).
*Petal color, lower surface*.—RHS NN155C (white group).
*Petal average length* (*mm*).—12.1.
*Petal average width* (*mm*).—13.3.
*Petal average length/width ratio*.—0.91 (broader than long).
*Average petal quantity per flower*.—5.6.
*Petal shape*.—Obovate.
*Petal texture*.—Smooth.
*Petal shape of base*.—Obtuse.
*Petal shape of apex*.—Rotund.
*Petal margins*.—Entire (smooth).
*Sepal color, upper surface*.—RHS 137A (green group).
*Sepal color, lower surface*.—RHS 138A (green group).
*Sepal average length* (*mm*).—10.8.
*Sepal average width* (*mm*).—5.7.
*Sepal average length/width ratio*.—1.89.
*Average sepal quantity per flower*.—11.8.
*Sepal shape*.—Elliptical.
*Sepal texture*.—Light.
*Sepal shape of apex*.—Acute.
*Sepal margins*.—Ranges from entire (smooth) to acute (serrated).
*Flower bud color*.—RHS 145B (yellow green group).
*Flower bud shape*.—Cup.
*Flower bud average length* (*mm*).—12.6.
*Flower bud average diameter* (*mm*).—7.6.
*Corolla average diameter* (*mm*).—31.2 (medium).
*Flower average depth* (*mm*).—9.9 (ranges from shallow to medium).
*Calyx average diameter* (*mm*).—29.3.
*Size of calyx relative to corolla*.—Ranges from smaller to same size.
*Arrangement of petals*.—Overlapping.
*Size of inner calyx relative to outer calyx*.—Same.

Reproductive organs:
*Anther color*.—RHS 15A (yellow orange group).
*Filament color*.—RHS 145C (yellow green group).
*Filament average length* (*mm*).—1.6.
*Anther average length* (*mm*).—1.4.
*Anther average width* (*mm*).—1.0.
*Anther shape*.—Elliptic.
*Pollen amount*.—Abundant.
*Ovary color*.—RHS 148C (yellow green group).
*Style color*.—RHS 151C (yellow green group).
*Pistil average quantity per flower*.—349.
*Pistil average length* (*mm*).—1.1.
*Style average length* (*mm*).—1.0.
*Stigma average diameter* (*mm*).—0.2.
*Stigma shape*.—Rounded.

Disease and pest reactions:
*Powdery mildew* (*sphaerotheca macularis*).—Susceptible.
*Botrytis fruit rot* (*botrytis cinerea*).—Moderately susceptible.
*Fusarium wilt* (*fusarium oxysporum*).—Resistant.
*Two-spotted spider mite* (*tetranychus urticae*).—Moderately susceptible.

We claim:

1. A new and distinct strawberry plant named 'PE-14.145.059', as herein described and illustrated by the characteristics set forth above.

* * * * *